United States Patent [19]

Raemer et al.

[11] 4,211,239
[45] Jul. 8, 1980

[54] NEONATAL OXYGEN CONSUMPTION MONITOR

[75] Inventors: Daniel B. Raemer; Dietrich K. Gehmlich; Dwayne R. Westenskow, all of Salt Lake City, Utah; Curtis C. Johnson, deceased, late of Salt Lake City, Utah, by Charles W. Whitehead, Wilma W. Johnson, personal representatives

[73] Assignee: University of Utah, Salt Lake City, Utah

[21] Appl. No.: 902,471

[22] Filed: May 3, 1978

[51] Int. Cl.$^2$ .................. A61H 1/00; A61M 16/00
[52] U.S. Cl. ........................................ 128/716; 128/718
[58] Field of Search ............... 128/716, 718, 720, 725, 128/146.4, 148.5

[56] References Cited

U.S. PATENT DOCUMENTS

| | | | |
|---|---|---|---|
| 2,707,947 | 5/1955 | Traugott | 128/718 |
| 3,035,569 | 5/1962 | Dubsky et al. | 128/718 |
| 3,611,801 | 10/1971 | Fagot et al. | 128/716 |
| 3,698,384 | 10/1972 | Jones | 128/718 |
| 3,898,987 | 8/1975 | Elam | 128/716 |

Primary Examiner—Willis Little
Attorney, Agent, or Firm—Thorpe, North & Gold

[57] ABSTRACT

An oxygen consumption monitor system suitable for use in measuring oxygen uptake in neonates wherein the system includes a check valve system in combination with a high flow, positive-end-expiratory-pressure respirator for supplying a high volume, controlled flow of oxygen through a flow circuit which includes (1) a primary flow line for carrying most of the oxygen supply through a respirator circuit maintained at a positive pressure, and (2) a secondary outlet communicating from said primary flow line through the check valve combination to permit inspiration of oxygen from the respirator circuit and expiration to a separate chamber for measurement of oxygen consumption. Minimal deadspace is developed in the check valve combination to insure fresh oxygen supply with each inspiration by the neonate. The use of opposing oneway valves at inlet and outlet locations of the valve combination permits use of a single opening for coupling to an endotrachael tube. The reduced deadspace also enables accurate oxygen consumption measurement by cumulating the amounts of oxygen required to replenish the expired air to an oxygen concentration measured in the primary flow line.

12 Claims, 7 Drawing Figures

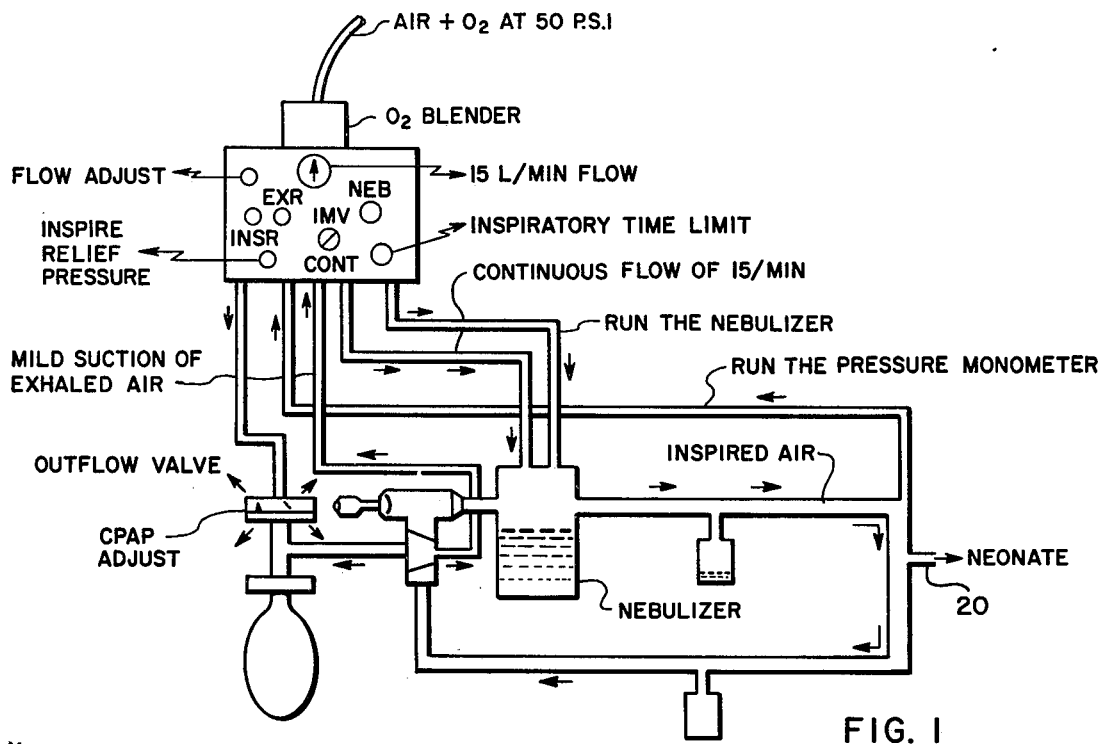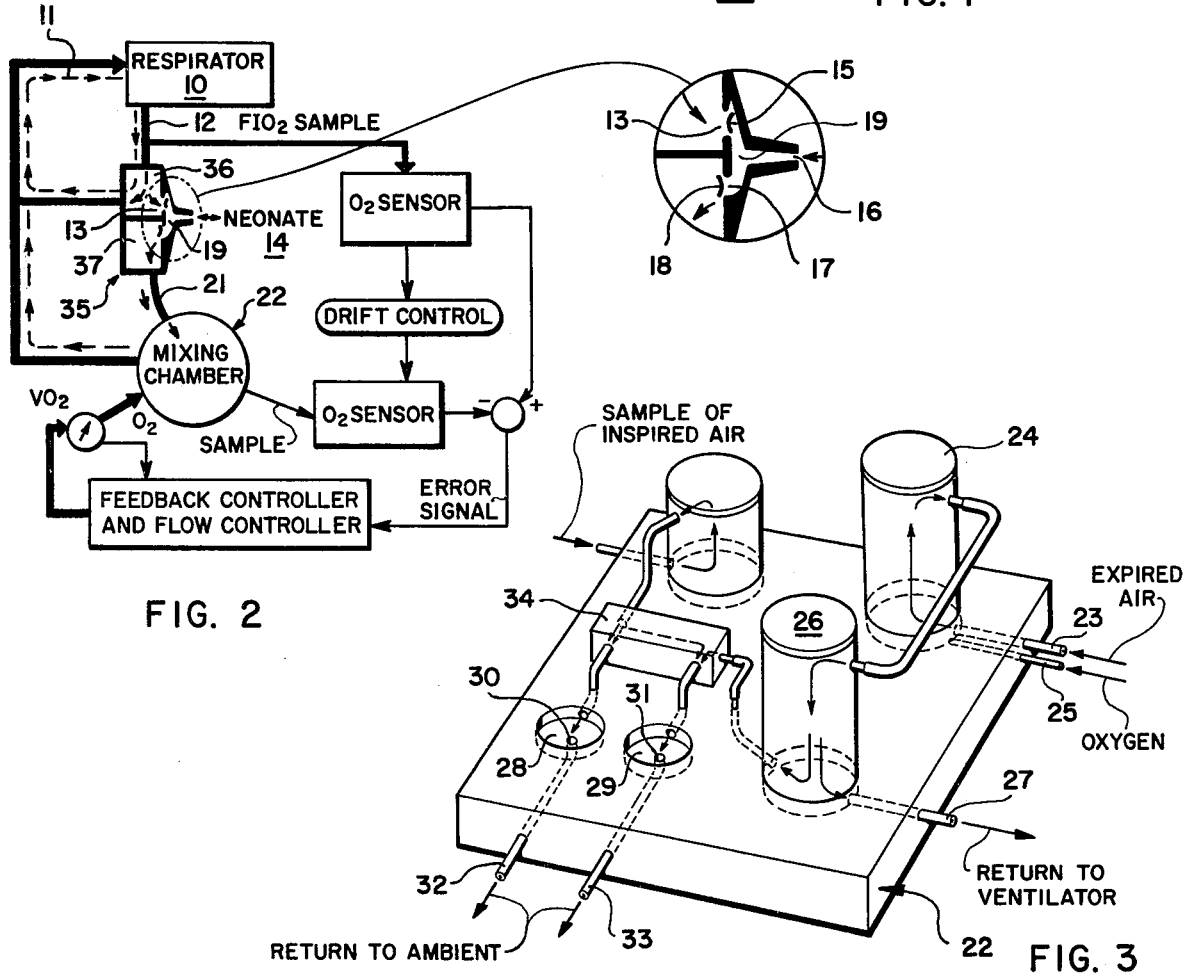

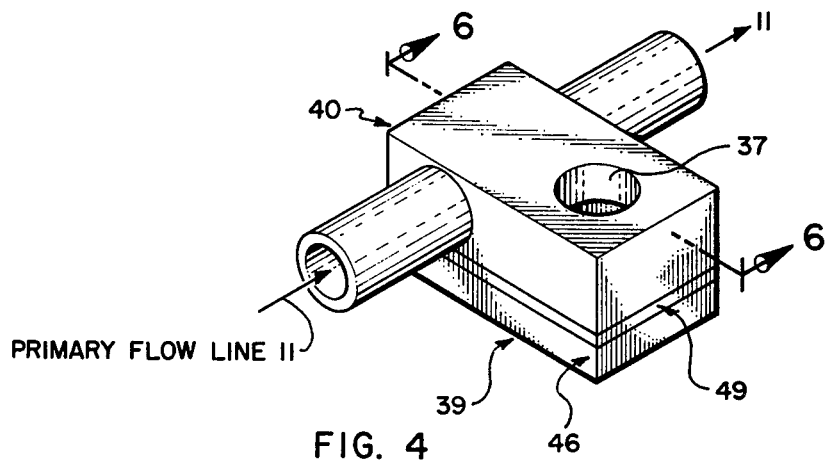
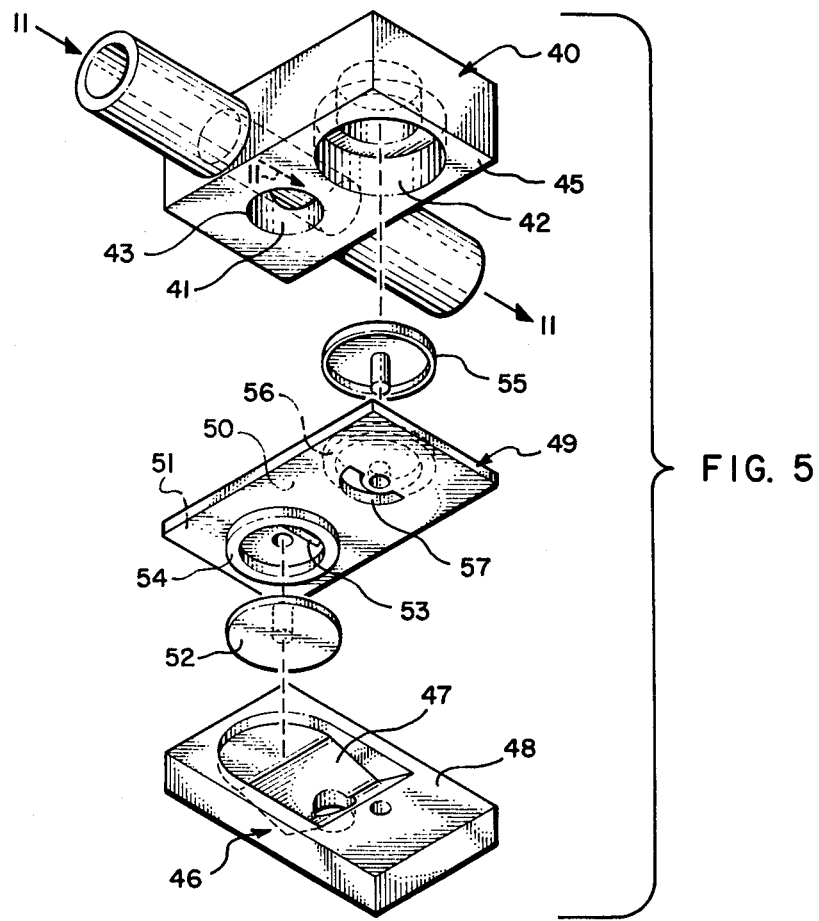

NEONATAL OXYGEN CONSUMPTION MONITOR

The invention described herein was made in the course of work under a grant from the National Institute of Health, Department of Health, Education and Welfare.

BACKGROUND OF THE INVENTION

1. Field of the Invention

This invention relates to respiratory systems useful in supplying oxygen to neonates, and more particularly to apparatus for measuring oxygen uptake in such systems.

2. Prior Art

In situations where premature or term infants less than one year of age require ventilatory support, special problems occur unique from the conventional systems used for adult respiration. Since the breath volume changes are much smaller in neonatal systems (0.7–2.7 liters per minute), previous methods for controlling system gain response have not been easily adaptable. Furthermore, the high respiratory rate (20–60 per minute) and low tidal volume (7–10 ml/kg) of neonates create additional problems in design for a neonatal respirator with oxygen consumption monitoring capability.

Further limitations rise with respect to those infants having Respiratory Distress Syndrome (RDS) inasmuch as such infants must always be kept under Continuous Positive Airway Pressure (CPAP), usually in a range of 3–5 mm Hg. CPAP is necessary in such cases to increase functional residual capacity, to improve compliance of the lung, and to prevent atelectasis. In severe RDS and RDS with pneumonia, the neonate is generally kept on CPAP and also on Intermittant Mandatory Ventilation (IMV). In addition to meeting the aforementioned requirements, an effective neonatal ventilation system must also provide a high flow of oxygen enriched air (5–15 liters per minute) directed past the endotracheal tube of the infant so that he always inspires fresh air.

FIG. 1 illustrates a positive-end-expiratory-pressure respirator which has the capability to incorporate CPAP and CPAP-IMV modes and to provide a high flow of oxygen enriched air through a respirator loop. No provision is made, however, for separate retrieval of expired air from the neonate so that oxygen consumption can be effectively monitored. Instead, both inspiration and expiration occur through the same tube opening 20 to the neonate with the expired volume of air re-entering the primary flow line of the high flow oxygen circuit. The eventual return of expired air to the flow line is essential in such units in order to preserve a constant positive pressure throughout the ventilatory system. Therefore, because of an intermittent addition of small volumes of expired air to the continuous high rate of flow and high oxygen content in this primary flow line, a comparison of oxygen content before and after inspiration has not been practical.

Numerous benefits could be realized by a ventilatory system which permits measurement of oxygen consumption or uptake by neonates. Metabolic rate, for example, can be usefully monitored since it directly relates with oxygen consumption. Previously, metabolic rate has been determined by means of skin temperature probes which detect the environmental temperature within the incubator. The obvious time lag and potential inaccuracy of this method suggest that a substantial benefit would arise with a technique of direct measurement of oxygen consumption. An additional need for measurement of oxygen consumption arises with infants having a pulmonary disease who must be ventilated with an increased inspired oxygen fraction $F_{IO_2}$. Too high a $F_{IO_2}$ can be highly toxic and damaging to the lungs. By monitoring the extent of oxygen uptake, the value for $F_{IO_2}$ can be reduced to an optimum level, without endangering the infant.

Infants having RDS which are ventilated under CPAP may experience a condition referred to as alveolar recruitment, as well as the aforementioned increase in lung compliance and functional residual capacity. At present, the CPAP settings on a respiratory system for neonates are arbitrary and must be obtained by trial and error. If the CPAP is set at high levels, it may cause alveolar overdistension or may even decrease the compliance of the lungs and also decrease the alveolar ventilation, so that the infant breathes harder in order to maintain alveolar ventilation. By monitoring oxygen consumption at different CPAP levels, the optimal airway pressure can be determined to avoid the aforementioned adverse side effects.

Finally, infants with severe RDS, RDS with pneumonia, bronchopulmonary dysplasia, etc., have to be managed with CPAP and Intermittent Mandatory Ventilation (IMV). The selection of optimal IMV settings on the respirator is very difficult since there are many parameters to be taken into account, such as air way pressure, inspiratory-expratory rate, IMV and CPAP. At present, the CPAP-IMV settings are obtained through trial and error by blood gas analysis on the infant. Monitoring of oxygen consumption would provide a more direct analysis for the optimal conditions and settings.

OBJECTS AND SUMMARY OF THE INVENTION

It is therefore an object of the subject invention to provide a ventilatory system for neonates which is adapted for measuring oxygen uptake.

It is a further object of this invention to provide apparatus for an oxygen consumption monitor system using a high flow, positive-end-expiratory-pressure respirator for supplying high volume, controlled oxygen flow.

It is an additional object of this invention to provide a valve system for enabling ventilation assist to neonates.

It is another object of this invention to provide a valve system capable of separating expired air for measurement of oxygen uptake.

A still further object of this invention is to provide a valve suitable for use with an oxygen consumption monitor system for neonates in which the amount of dead space within the valve system is minimized.

These and other objects of the present invention are realized in an oxygen consumption monitor system adapted for use in measuring oxygen uptake in neonates wherein a high flow, positive-end-expiratory-pressure respirator is utilized for supplying a controlled flow of oxygen. The system includes a flow duct for conducting oxygen from the respirator along a primary flow line. This flow duct includes a secondary outlet which communicates from the primary flow line to a one way inlet valve which forms part of an inlet and outlet check valve combination. Upon inspiration by the neonate, oxygen is drawn from the primary flow line through the inlet valve into a respiration duct which leads to the lungs of the neonate. Upon expiration, the inlet valve seats, blocking air passage return to the primary flow line. The expired air therefore vents through an outlet check valve to an expiration duct which conducts the expired air to an oxygen sensor utilized in the measurement of the extent of oxygen uptake. By coupling the inlet and outlet check valve combination between (1) the respiration duct on one side and (2) the respective openings of the secondary outlet and expiration duct on the other side, dead space is minimized and system accuracy is improved.

Other objects and features will be obvious to a person skilled in the art from the following detailed description, taken with the accompanying drawings.

DESCRIPTION OF DRAWINGS

FIG. 1 is a flow diagram illustrating a respirator currently used in connection with ventilation of neonates.

FIG. 2 shows a block diagram illustrating the oxygen consumption monitor and ventilation system utilized in accordance with the subject invention.

FIG. 3 illustrates one embodiment for the mixing chamber utilized with the subject oxygen consumption monitor.

FIG. 4 is a perspective view of an opposing check valve system used with the subject invention.

FIG. 5 is an exploded view of the check valve system shown in FIG. 4, looking up at the top two sections and down at the bottom section.

DETAILED DESCRIPTION OF THE INVENTION

Figure 6:
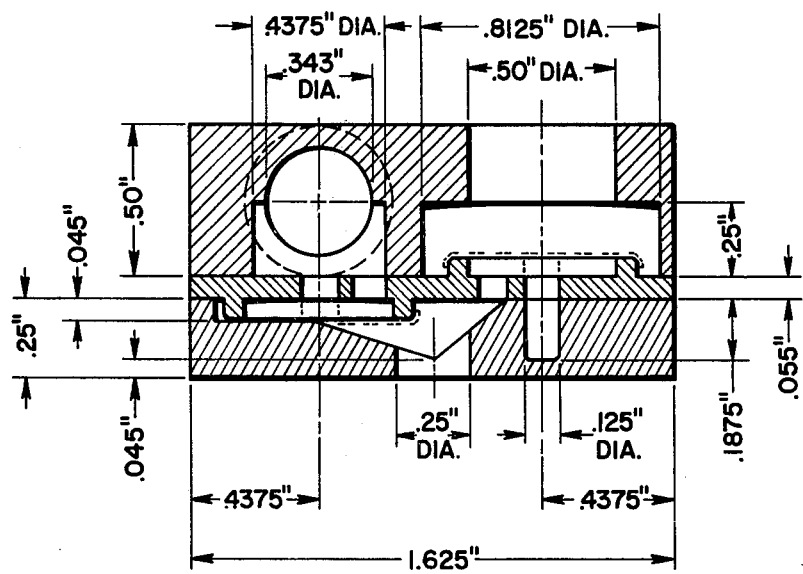
FIG. 6 shows a cross section view taken along lines 6—6 of FIG. 4, with flexible flap removed, and includes dimensional specifications.

Referring to the drawings:

The basic operation of an oxygen consumption monitor system for measuring uptake of oxygen in neonates is illustrated in FIG. 2. A respirator 10 having capabilities for CPAP and CPAP-IMV is utilized to establish a primary flow line as illustrated by the broken line circuit 11. This monitor system may be adapted for use with any high flow, positive-end-expiratory-pressure respirator; however, the respirator shown in FIG. 1, known as the BABY BIRD respirator, has proven very effective.

The primary flow line circuit 11 includes a flow duct 12 which constitutes the first leg of the circuit. This flow duct 12 communicates with a secondary outlet 13 which permits oxygen flow to the neonate 14 on inspiration. This outlet 13 is referred to as a secondary outlet in view of the noninterrupting action thereof with respect to the primary flow line 11. The function of the primary flow line is to provide a reservoir of fresh oxygen which may be maintained at a substantially constant pressure slightly above atmospheric pressure.

Flow through the secondary outlet 13 is controlled by a one way inlet valve 15 which permits flow thereby upon inspiration of the neonate 14. Such inspiration causes flow of fresh oxygen from the primary flow line 11 through the inlet valve 15, to the valve opening 16 which connects to a respiratory duct (not shown). This respiratory duct may be an endotracheal tube with attached cuff or other appropriate means for conveying oxygen to the lungs of the neonate.

Upon expiration by the neonate, air flow passes from the respiratory duct, through the valve opening 16 and through an outlet 17. Flow through the subject outlet 17 is controlled by a one way valve 18. It is necessary that each of the respective one way inlet and outlet valves 15 and 18 is biased in a seated position at the respective inlet 13 and outlet 17 openings. Such a configuration provides unidirectional flow upon inspiration through the inlet valve 15 and opposite unidirectional flow upon expiration through the outlet valve 18.

Chamber 19 contained between the respective inlet and outlet valves 15 and 18 and the valve opening 16 should be made as small as possible to avoid excessive deadspace. Such deadspace results in rebreathing by the infant of expired air, thereby decreasing the oxygen supply to the infant. Such deadspace develops error in oxygen uptake measurements and generally disrupts the effectiveness of the ventilating system. The deadspace problem discussed herein is less serious in the structure of FIG. 1 because of the absence of flow-controlling valves at the respirator opening 20.

During expiration by the neonate, flow through the valve outlet 17 continues to an expiration duct 21 which conducts the expired air to a mixing chamber 22, in preparation for analysis of the amount of oxygen consumed. This mixing chamber and associated oxygen consumption monitoring components are illustrated in block format in FIG. 2 and in the structural embodiment of FIG. 3. Referring to these respective illustrations, it will be noted that expired air is delivered to an inlet 23 opening to a first canister 24 which contains a $CO_2$ scrubber for removal of $CO_2$ exhalant. Also introduced at the first canister 24 through inlet 25 is a replenishing oxygen component for mixing and delivery to a second canister 26 for drying. Most of the dried air mixture is returned through outlet 27 to the primary flow line 11 and respirator 10. The amount of oxygen sent to the first canister through inlet 25 is determined by readings taken at a pair of oxygen sensors 28 and 29 which comparatively analyze samples from the primary flow line 11 and drying canister 26.

To accomplish the comparison of oxygen content of inspired air versus expired air, samples are drawn from each fraction and are exposed to a respective polaragraphic oxygen sensor 28 or 29. The sensor space therein is vented to the outside through a relatively large orifice 30 and 31 to provide a negligible pressure drop across the sensors. A pair of controlled leak paths 32 and 33 do not disrupt the constant positive pressure developed within the system because of the small amount of leakage which occurs.

As is more particularly shown in FIG. 3, the mixing chamber circuit also has a feature which allows dried, inspired gas to leak past both oxygen sensors 28 and 29 (shown as dotted paths through the solenoid valves 34), while excluding expired gas by means of a three-way control valve. This configuration is utilized to calibrate the sensors by simultaneously exposing them to the same fraction of inspired air and then electronically storing the error due to drift of either or both of the oxygen sensors. This error is later utilized to adjust oxygen replenishment to a more correct value. In FIG. 2 this arrangement is represented by the blocked item entitled Drift Control which includes an error detecting sample-and-hold device.

The amount of oxygen introduced at the first canister inlet 25 is determined by the amount of error signal occurring between the pair of oxygen sensors (See FIG.

2). By means of proportional plus integral control, a precision oxygen flow controller (Brook Instruments) adds a measured flow of oxygen until a null reading is obtained between the respective inspiration and expiration fractions of oxygen.

As has been mentioned previously, an important feature of the subject invention is the utilization of a valve system which incorporates minimal dead space while preserving a positive pressure throughout the respiratory circuit, along with opposing unidirectional inspiration and expiration flow. These characteristics are illustrated in a general valve configuration shown in FIG. 2. This configuration is represented by the three chamber housing 35 in which a first chamber 36 is coupled into the primary flow line circuit 11. A second chamber 37 is coupled to the expiration duct 21 which leads to the mixing chamber 22. The third chamber 19 is independently coupled to each of the first and second chambers 36 and 37 and further includes the valve opening 16 which leads to the lungs of the neonate. It is important that the volume of this third chamber be minimal to avoid deadspace and the attendant problems therewith.

The three chambers are separated by means of one way valves which establish the opposing unidirectional oxygen flow to and from the neonate. These valves have been previously discussed and are identified as an inlet valve 15 and an outlet valve 18.

A preferred structural embodiment for the three chambered housing is illustrated in FIGS. 4 through 7. In these figures, an inlet and outlet check valve combination is formed by a three part housing 39. Referring to FIG. 5, the first housing section 40 contains cavities representing the first and second chambers 41 and 42 previously discussed. The first chamber 41 includes a portion of the primary flow line 11 and the previously referenced secondary opening 43 from the primary flow line. This secondary opening 43 operates as an additional opening from the primary flow line 11 in order to establish a flow path for fresh air to the neonate. In addition, the first housing section includes a contacting face 45 which operates to seal against the remaining housing section to partially enclose the first and second chambers, which open at the contacting face for exposure thereof to the inlet and outlet check valves.

The third chamber previously referenced is formed in the second housing section 46. This chamber consists of a thin channel recess 47 located at a contacting face 48 of said second housing section. This thin channel recess 47 is designed to have minimal volume to avoid unnecessary deadspace. The recess 47 extends along a specific length of the contacting face 48 to permit placement thereof over a portion of each of the contacting face openings 41 and 42 of the first housing section 40. This configuration enables joint coupling of the first and second chambers to the third chamber.

A third section of housing 49 is sandwiched between the first and second housing sections and consists of a plate-like member having opposing faces 50 and 51. This third section includes inlet valve 52 biased in a seated position with respect to an opening 53 through said plate member 49. The inlet valve 52 is seated at a ridged portion 54, enclosing the plate opening 53 such that only unidirectional flow from the primary flow line 11 is permitted. This inlet flow is actuated by inspiration of the neonate.

An outlet check valve 55 is likewise attached at the third housing section 49 and is biased in a seated position at a ridged portion 56 on the opposite side of this third section 49, the ridged portion enclosing an expiration opening 57. This valve 55 is attached at the opposing side of the housing section 49 to enable reverse unidirectional flow upon expiration of the neonate and is aligned with the expiration duct opening 42 to permit expiration of the infant into the mixing chamber for analysis of oxygen consumption.

With the three sections of the valve housing attached at the opposing contacting faces of the first and second housing sections, all air flow to and from the neonate is confined through the respective three chambers as previously described. The chamber sizes may be of different configurations and volumes; however, a preferred structural summary has been provided in FIGS. 6 and 7 as illustrative of the preferred embodiment. Although the volumes of the first and second chambers are not critical, the volume of the third chamber is significant because it represents a deadspace developed within the valve combination. Its volume can therefore be reduced to a minimum to avoid the adverse effect previously disclosed. A maximum volume of 2.0 cc may be operable; however, the preferred volume for this third chamber is approximately 1.0 cc.

Figure 7:
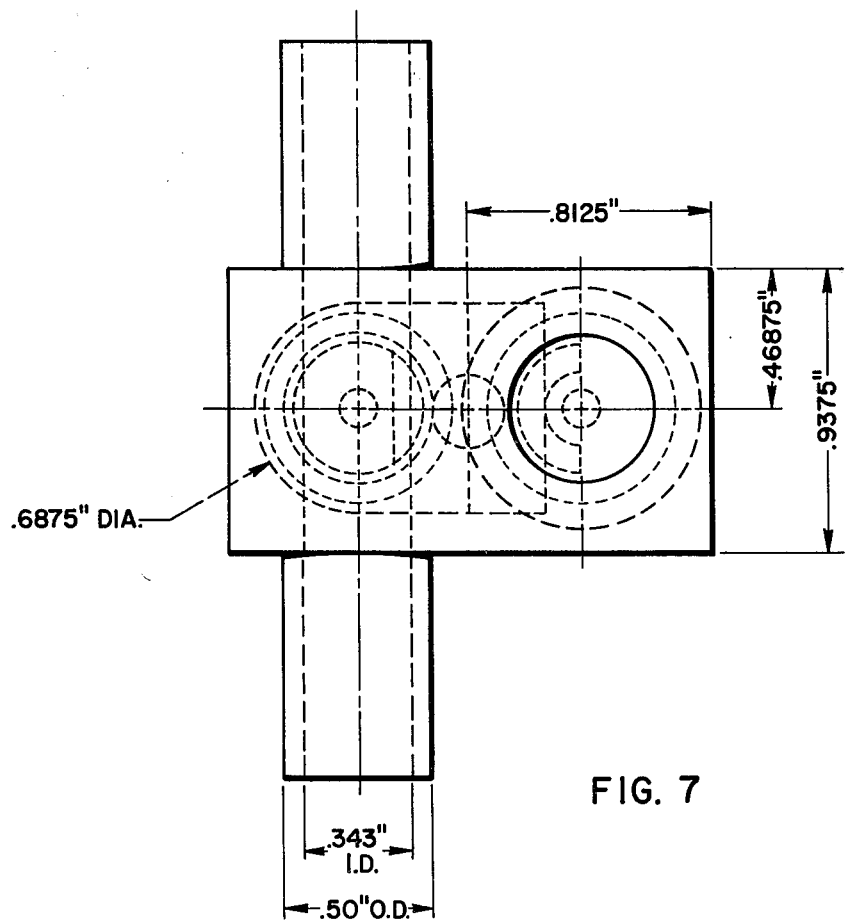
FIG. 7 is a top view of FIG. 4, also including dimensional specifications.

FIGS. 6 and 7 illustrate the specifications used in one embodiment which provides a 1.0 cc volume for the third chamber. The inlet and outlet check valves are shown only in phantom lines, since such valves are commercially available.

Numerous materials are available for construction, including plastics which can be injection molded to the appropriate configuration. The selection of valve material should be limited to highly pliable materials such as standard respiratory valve flaps. It is important to maintain the lowest possible resistance to air flow to avoid extra effort required during respiration by the neonate. Valves utilized with the subject embodiment were standard ⅜ inch respiratory valves and offered very little resistance during ventilatory support.

Tests utilizing the preferred embodiment disclosed herein have shown highly favorable results when applied to neonatal ventilatory systems. In a series of 36 experiments, for example, a mean $VO_2$ measurement error of only 3% was experienced from the standard comparison of measured $VO_2$ versus ideal $VO_2$. This corresponds to a correlation coefficient between these calculated and observed $VO_2$ values of 0.995 and a mean squared deviation from regression of only 8.56 cc/minute. The system response experienced was in the order of 20 seconds.

The primary uses and advantages of the subject invention include the following:

1. The neonatal oxygen monitor allows oxygen uptake to be dynamically determined in an open or closed pressure breathing circuit.

2. Oxygen uptake is determined by a replenishment technique which avoids the use of spirometers, flow meters, or any other volume, flow, or pressure measuring device in the patient gas stream.

3. Once the instrument has reached steady state, the oxygen uptake can be measured continuously and indefinitely.

4. The feedback technique used makes it unnecessary to determine gas concentrations with any absolute accuracy because oxygen concentration signals are nulled to obtain the oxygen utilization data.

5. The system provides a means to mix the expired gas with oxygen, remove $CO_2$ and water vapor, and provide a small sample leak to an oxygen sensor. This system allows for accurate measurements under a variety of flows, pressures, breathing patterns, and therapeutic maneuvers without interference.

6. The low dead space valve is a unique means of directing all expired gas to the measurement system without providing excessive expiratory or inspiratory resistance or dead space to the infant.

As previously indicated, although previous forms have been herein described, it needs to be understood that the present disclosure is by way of example and that variations are possible without departing from the scope of the hereinafter claimed subject matter, which subject matter is to be regarded as the invention.

We claim:

1. An oxygen consumption monitor system suitable for use in measuring oxygen uptake in neonates, comprising:
   (a) a respirator for supplying a high volume, controlled flow of oxygen;
   (b) a flow duct for conducting said oxygen from the respirator, said flow duct having a primary flow line and a secondary outlet communicating with said primary flow line;
   (c) a respiration duct having one end adapted for communication with the lungs of said neonate;
   (d) an expiration duct for receiving expired gas from the neonate;
   (e) an inlet and outlet check valve combination coupled jointly on one side of said valves to said respiration duct and on the other side respectively to said secondary outlet and said expiration duct, said valve combination coupling providing an intermittent inspiration passageway from said primary flow line, through said inlet check valve and into the respiration duct and lung region, and an exiration passageway through said respiration duct and outlet check valve to said expiration duct, each of said inlet and outlet valves being biased in a closed position, the valve combination coupling having minimal deadspace; and
   (f) means coupled to said primary flow line and said expiration duct for comparing the oxygen concentration of inspired gas versus that of corresponding expired gas for a determination of the amount of oxygen consumed.

2. An oxygen consumption monitor system as defined in claim 1, wherein said respirator comprises a high flow, positive-end-expiratory-pressure respirator.

3. An oxygen consumption monitor as defined in claim 1, wherein said check valve combination comprises a three chamber housing including:
   a first chamber adapted to communicate with a primary flow line of gas supplied within said respiratory system;
   a second chamber adapted for coupling to an expiration duct within said oxygen consumption monitoring circuit;
   a third chamber independently coupled to each of said first and second chambers by means of opposing one way valves and having a third opening adapted for coupling to a respiratory duct connected to a patient;
   said first and third chambers being coupled by an inlet valve which permits flow to said third chamber but checks counter flow therebetween, said second and third chambers being coupled by an outlet valve which permits flow from said third chamber to said second chamber but checks counter flow therebetween, both valves being biased in a closed position; and
   a chamber volume of said third chamber substantially less than either of the first or second chamber volumes.

4. An oxygen consumption monitor as defined in claim 1, wherein said first chamber has openings for cross flow of said primary flow line therethrough, causing direct communication between said inlet valve and said primary flow line.

5. An oxygen consumption monitor as defined in claim 1, wherein:
   said first and second chambers are formed as cavities in a first housing section having a contacting face, said first chamber being adapted for coupling into the primary flow line and having an additional opening at the contacting face of said section;
   said second chamber opens at said contacting face and has means for coupling an expiration duct thereto;
   said third chamber is formed by a thin channel recess at a contacting face of a second housing section, which recess extends along a sufficient length of said contacting face to permit placement thereof over a portion of each of said contacting face openings of said first housing section, thereby permitting joint coupling of said first and second chambers to said third chamber, said third chamber further comprising an opening from said recess which is adapted for coupling to a respiration duct;
   said contacting faces of the first and second housing sections being adapted for sandwiching opposing faces of a third section of housing comprising a platelike member having inlet and outlet valves disposed therein at locations corresponding to the coupling locations of said respective first and second chamber openings with said third chamber.

6. An oxygen consumption monitor as defined in chaim 1, wherein the volume of said third chamber is less than 2 cc.

7. An oxygen consumption monitor as defined in claim 1, wherein the volume of said third chamber is approximately 1.0 cc.

8. An oxygen consumption monitor as defined in claim 1, wherein said inlet and outlet valves include rubber flap valves which rest in a seated position at said sandwiched plate section during expiration and inspiration respectively.

9. An oxygen consumption monitor as defined in claim 1, wherein said oxygen concentration comparison means comprises a pair of oxygen sensors which respectively measure and compare oxygen concentrations in said primary flow line and in a mixing chamber coupled to said expiration duct, said mixing chamber further comprising feed means for introducing oxygen therein at a controlled rate based on a measured deficiency of oxygen in said mixing chamber as compared to said primary flow line oxygen concentration.

10. An oxygen consumption monitor as defined in claim 9, further comprising a $CO_2$ scrubber and dryer coupled to said mixing chamber and operable to remove $CO_2$ and water from the expired gas prior to exposure thereof to said oxygen sensor.

11. An oxygen consumption monitor as defined in claim 10, further comprising a return duct coupled between said mixing chamber and said respirator for returning said expired gas to the respirator to thereby maintain a constant pressure within the system.

12. A method for measuring oxygen uptake in neonates ventilated by a positive-end-expiratory-pressure respiratory system, comprising the steps of:
   a. interposing a one way inlet check valve at a secondary opening to a primary oxygen flow line, thereby permitting flow therethrough from said primary flow line;
   b. coupling said inlet valve to a low volume chamber having a first outlet means to a respiratory duct communicating with the lungs of said neonate and a second outlet means coupled to an expiration duct for conducting expired air to an oxygen comparison sensing system for effecting replenishment of said expired air, said second outlet means including one way valve means for precluding flow therethrough except during expiration by the neonate, said inlet check valve being biased in the closed position during such expiration;
   c. analyzing respective samples of inspired and expired air within the system for oxygen concentration;
   d. replenishing depleted oxygen to the expired air based on the difference of oxygen concentration detected with respect to the inspired sample; and
   e. returning the replenished air to the respirator to maintain a constant positive-pressure system.

* * * * *